(12) United States Patent
Merle et al.

(10) Patent No.: US 9,744,048 B2
(45) Date of Patent: Aug. 29, 2017

(54) PROSTHESIS FOR THE RESTORATION OF A JOINT BETWEEN TWO BONES, AND ANCILLARY TOOL FOR THE ASSEMBLY THEREOF

(71) Applicant: BIOVER, Hergiswil (CH)

(72) Inventors: Michel Merle, Luxembourg (LU); Beat Leu, Buochs (CH)

(73) Assignee: BIOVER A.G., Hergiswil (CH)

( * ) Notice: Subject to any disclaimer, the term of this patent is extended or adjusted under 35 U.S.C. 154(b) by 55 days.

(21) Appl. No.: 14/424,450

(22) PCT Filed: Aug. 8, 2013

(86) PCT No.: PCT/IB2013/001757
§ 371 (c)(1),
(2) Date: Feb. 27, 2015

(87) PCT Pub. No.: WO2014/033516
PCT Pub. Date: Mar. 6, 2014

(65) Prior Publication Data
US 2015/0223942 A1    Aug. 13, 2015

(30) Foreign Application Priority Data
Aug. 29, 2012    (FR) ...................... 12 02321

(51) Int. Cl.
*A61F 2/38*    (2006.01)
*A61F 2/42*    (2006.01)
(Continued)

(52) U.S. Cl.
CPC .......... *A61F 2/4241* (2013.01); *A61F 2/4637* (2013.01); *A61F 2002/30393* (2013.01);
(Continued)

(58) Field of Classification Search
CPC ...... A61F 2220/0025; A61F 2220/0033; A61F 2/4241; A61F 2002/30563; A61F 2/4637;
(Continued)

(56) References Cited

U.S. PATENT DOCUMENTS 3,946,446 A    3/1976  Schofield
5,011,497 A *  4/1991  Persson ................. A61F 2/4241
                                                623/21.15
(Continued)

FOREIGN PATENT DOCUMENTS

FR    2634373 A1    1/1990

OTHER PUBLICATIONS

International Search Report, dated Nov. 5 2013, from corresponding PCT application.

*Primary Examiner* — Christopher D Prone
(74) *Attorney, Agent, or Firm* — Young & Thompson

(57) ABSTRACT

A prosthesis includes a first and second plate; elements for mounting the plates to pivot about an axis, which include a flexible hinge including a cylindrical plane flexible strip with two cylindrical swellings respectively associated with two edges of the strip, the dimension of the cross-sections of the swellings, taken in a direction perpendicular to the plane containing the pivot axis and passing through the swellings, being greater than the thickness of the strip taken in the same direction, a hole in each plate of shape complementary to the swellings and opening out in a first face of the corresponding plate; a slot made in each plate and opening out into the hole of that plate, in a second of its faces, and in the first face, the hinge and plates being mounted to so that the swellings and the strip are situated respectively in the two holes and slots.

8 Claims, 2 Drawing Sheets

(51) Int. Cl.
*A61F 2/46* (2006.01)
*A61F 2/30* (2006.01)
(52) U.S. Cl.
CPC .............. *A61F 2002/30626* (2013.01); *A61F 2002/30632* (2013.01); *A61F 2002/4243* (2013.01); *A61F 2002/4248* (2013.01); *A61F 2002/4251* (2013.01)
(58) Field of Classification Search
CPC .. A61F 2002/30626; A61F 2002/30393; A61F 2002/30632
See application file for complete search history.

(56) References Cited

U.S. PATENT DOCUMENTS

| | | | |
|---|---|---|---|
| 5,534,033 A | | 7/1996 | Simpson |
| 6,319,284 B1 * | | 11/2001 | Rushdy ................. A61F 2/4225 623/18.11 |
| 7,153,327 B1 * | | 12/2006 | Metzger ................... A61F 2/08 623/13.12 |
| 2010/0191342 A1 | | 7/2010 | Byrd et al. |

* cited by examiner

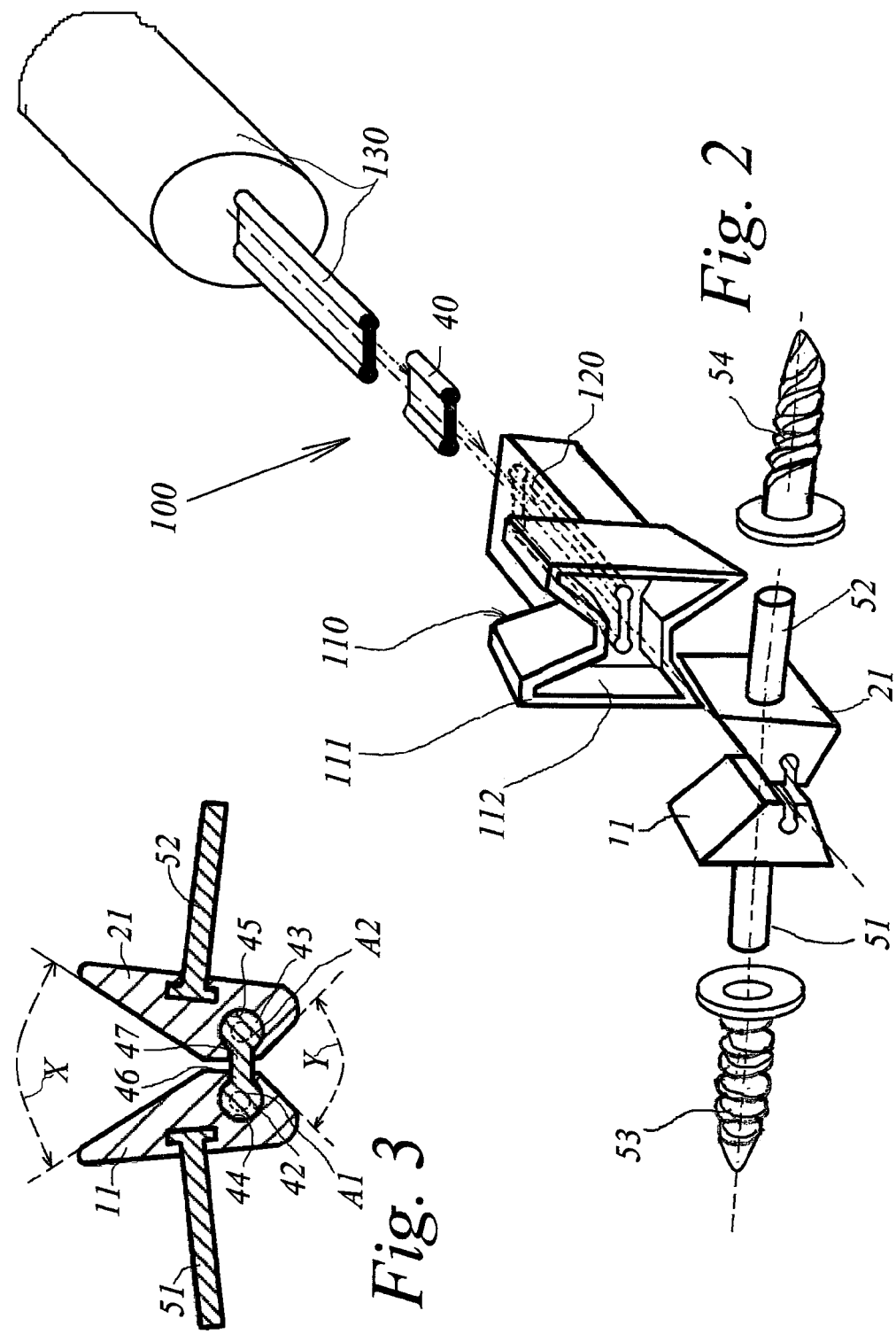

PROSTHESIS FOR THE RESTORATION OF A JOINT BETWEEN TWO BONES, AND ANCILLARY TOOL FOR THE ASSEMBLY THEREOF

BACKGROUND OF THE INVENTION

Field of the Invention

The present invention relates to prostheses for restoring a joint between two bones, which prostheses find a particularly advantageous but non-exclusive application as metacarpophalangeal and proximal interphalangeal joint prostheses.

The present invention also relates to an instrument for assisting in assembling such a prosthesis.

Description of the Related Art

Joint prostheses already exist, in particular for replacing metacarpophalangeal joints and proximal interphalangeal joints. By way of example such prostheses are described and shown in US 2010/191342, U.S. Pat. No. 3,946,446, U.S. Pat. No. 5,534,033, and FR 2 634 373.

Those known prostheses give good results, but present drawbacks due essentially to the complexity of their structure and thus the complexity of assembling them, and to the fact that their structure depends on the implantation technique used by the practitioner.

BRIEF SUMMARY OF THE INVENTION

An object of the present invention is thus to provide a prosthesis for restoring a joint between two bones, which prosthesis finds a particularly advantageous but non-exclusive application as a metacarpophalangeal joint prosthesis or as a proximal interphalangeal joint prosthesis, which prosthesis is of a structure that is very simple, easy to assemble and to implant, and that can also be implanted using numerous surgical approaches complying with the habits and the desires of practitioners who operate essentially via three approaches: dorsal, lateral, or via the palm, with these three approaches being the approaches most commonly adopted by surgeons.

More precisely, the present invention provides a prosthesis for restoring a joint between first and second bones, the prosthesis comprising:

a first plate;

means for associating this first plate with a resected end of the first bone;

a second plate;

means for associating this second plate with a resected end of the second bone; and means for mounting the two plates pivotally relative to each other about a pivot axis;

the prosthesis being characterized by the fact that the means for mounting the two plates pivotally relative to each other about the pivot axis are constituted by:

a flexible hinge, said flexible hinge comprising:

a plane flexible strip of substantially cylindrical shape;

two oblong swellings of substantially cylindrical shape; and means for associating these two oblong swellings respectively with two opposite edges of said flexible strip so that the generator lines of the cylindrical shapes of the strip and of the two swellings are substantially parallel to said pivot axis, the dimensions of the cross-sections of each of these two swellings respectively, taken in a direction perpendicular to the plane containing said pivot axis and passing through the two swellings, being greater than the thickness of said flexible strip taken in the same direction;

a hole made in each of the two plates, each hole having an end opening out in a first face of the plate in which it is made, the two holes having respective shapes complementary to the two respective swellings;

a slot made in each of the two plates, the slot made in a plate opening out into the hole made in that plate and into a second of the faces of said plate, and including an end opening out into the first face of the plate; and the flexible hinge and the two plates being mounted in cooperation in such a manner that the two swellings and the flexible strip are situated respectively in the two holes and in the two slots.

Another object of the present invention is to provide an instrument for assistance in assembling the above-defined prosthesis and characterized by the fact that it comprises:

a guide having one end including an indentation matching at least a portion of the two plates when they are in the position in which they are suitable for being associated by means of the flexible hinge;

a crosspiece made on either side in said guide and having a cross-section complementary to the cross-section of said flexible hinge, said crosspiece being made in said guide in such a manner as to be accurately in register with said ends of the holes and of the slots situated in the first faces of the two plates when the two plates are plugged into their respective indentations; and a pusher for pushing said flexible hinge in translation in said crosspiece in order to position said flexible hinge in cooperation with the two plates when the two plates are plugged into their respective indentations, in such a manner that the two swellings and the flexible strip are received respectively in the two holes and in the two slots.

BRIEF DESCRIPTION OF THE DRAWINGS

Other characteristics and advantages of the present invention appear from the following description given with reference to the accompanying drawings by way of nonlimiting illustration, in which:

FIG. 2 is a perspective and exploded view of the prosthesis of the invention matching the prosthesis shown in FIG. 1, and in cooperation with an embodiment of the instrument of the invention for assisting in assembling it; and FIG. 3 is a section view and a side view of a portion of another embodiment.

DETAILED DESCRIPTION OF THE PREFERRED EMBODIMENTS

Figure 1:
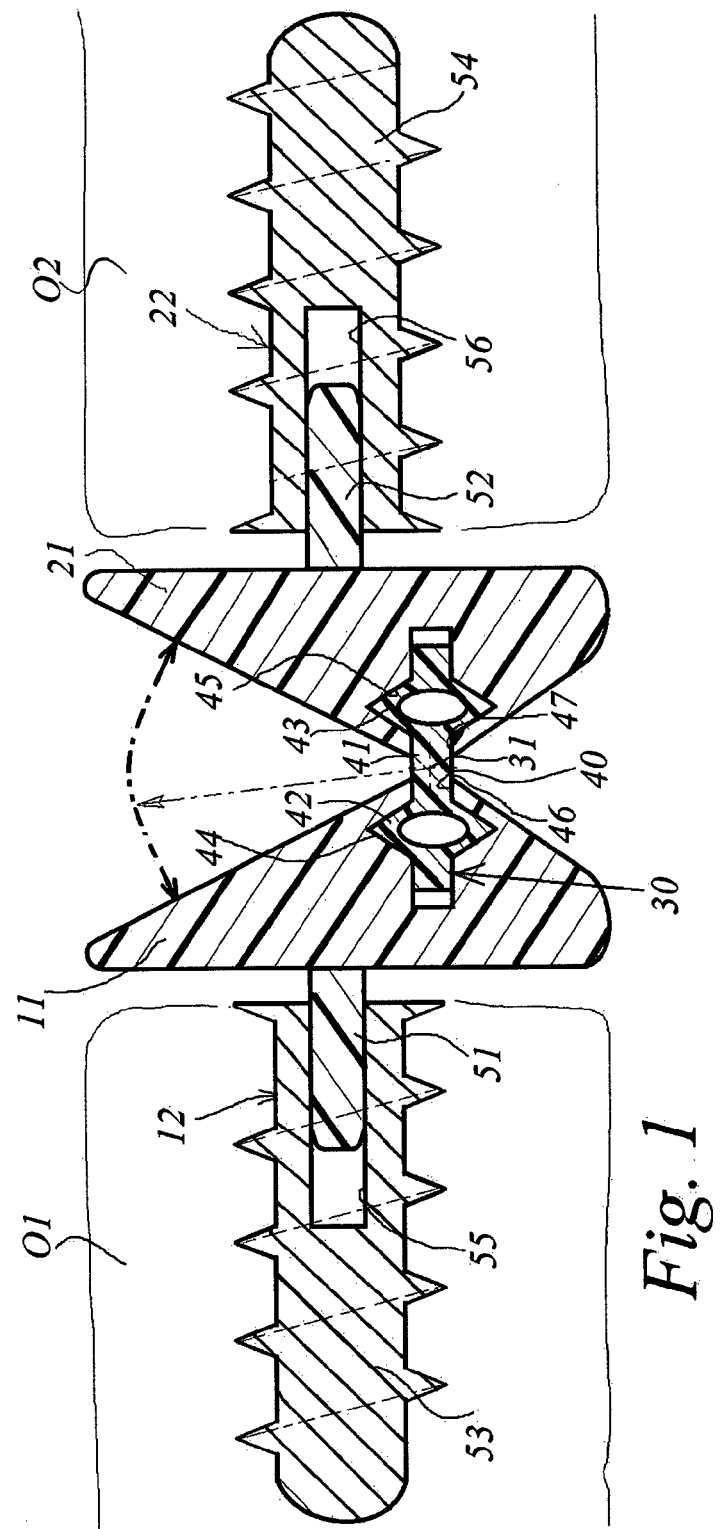
FIG. 1 is a section view and a side view of an embodiment of the prosthesis of the invention for restoring a joint between two bones.

It is specified that, in the present description, if the adverb "substantially" is associated with a term qualifying any given means, then that term may be understood either strictly or approximately.

The present invention relates to a prosthesis for restoring a joint between first and second bones O1, O2, e.g. a metacarpophalangeal joint or a proximal interphalangeal joint.

With reference to the three accompanying figures, the prosthesis comprises a first plate 11, means 12 for associating the first plate 11 with a resected end of the first bone O1, a second plate 21, means 22 for associating the second plate 21 with a resected end of the second bone O2, and means 30 for mounting the two plates 11, 21 to pivot relative to each other about a pivot axis 31.

According to a characteristic of the invention, the means 30 for mounting the two plates 11, 21 to pivot relative to each other about the pivot axis 31 are constituted by a flexible hinge 40 comprising a plane flexible strip 41 having a shape that is substantially cylindrical, two oblong swellings 42, 43 of substantially cylindrical shape, and means for associating the two oblong swellings 42, 43 respectively with two opposite edges of the flexible strip 41 so that the generator lines of the cylindrical shapes of the strip and of the two swellings are substantially parallel with the pivot axis 31, the dimensions of the respective cross sections of the two swellings 42, 43, taken in a direction perpendicular to the plane containing said pivot axis 31 and passing through the two swellings, being greater than the thickness of said flexible plate 41 taken in the same direction.

It is specified that the shapes of the two oblong swellings 42, 43 shown in the figures are given purely by way of illustration and that these oblong swellings could naturally have shapes that are substantially cylindrical, having any cross-section, e.g. circular, polygonal, etc., and optionally that are bodies of revolution.

Advantageously the two swellings 42, 43 of the strip 41 are made as a single piece, e.g. of preferably thermoplastic polycarbonate or the like, with the strip having a thickness determined so that it is both relatively flexible and springy, and also sufficiently strong not to break.

The prosthesis further includes a hole 44, 45 made in each of the two plates 11, 21, each hole having an end opening out in a first face of the plate in which it is made, the two holes 44, 45 having respective shapes complementary to the two respective swellings 42, 43. Preferably, the hole opens out at its two ends in two opposite first faces of the plate.

The prosthesis also includes a slot 46, 47 made in each of the two plates 11, 21, the slot made in a plate opening out into the hole made in that plate and into a second one of its faces, and including an end opening out into the first face of the plate. Preferably, the slot opens out at its two ends in two opposite first faces of the plate.

Furthermore, the flexible hinge 40 and the two plates 11, 21 are mounted in cooperation in such a manner that the two swellings 42, 43 and the flexible strip 41 are situated respectively in the two holes 44, 45 and in the two slots 46, 47.

The prosthesis may possibly include reinforcement embedded in the material from which the flexible hinge (40) is made, such as metal or analogous pins, e.g. for reinforcing the two swellings 42, 43.

By way of preferred example, the embodiment shown in FIG. 3 makes use of this possibility, the prosthesis having two cores A1, A2 shown in dashed lines, which cores are embedded respectively substantially in the middles of the swellings 42, 43 to ensure effective and durable retention of the swellings in the holes 44, 45.

Likewise, it is specified that this hinge 40 may also be made by means of a plurality of flexible materials, either in layers one on another, or else as a mixture of materials of different flexibilities. Depending on the results that are to be obtained, the person skilled in the art knows how to make a flexible hinge 40 that is suitable.

According to another characteristic of the invention that is most preferred, each plate is of cylindrical shape, its cross-section constituting the closed curve determining the cylindrical shape and defined perpendicularly to the generator lines, this curve having substantially the shape of a triangle with one of its vertices having an angle of value greater than ninety degrees, most advantageously an angle of value substantially equal to one hundred and two degrees. Under such conditions, the two triangles of the two plates are defined in such a manner that when the flexible hinge is not subjected to a bending force, and is thus at rest as shown in FIGS. 1 and 3, the two angles X and Y have values that are respectively equal substantially to sixty-five degrees and to ninety degrees.

In still more preferred manner, the slot 46, 47 made in each plate 11, 21 opens out substantially at one of the vertices of the above-defined triangle and is made along the height of the triangle passing via this one vertex.

In most advantageous manner, for ease of fabrication, cost reduction, and ease of management at all levels, the two plates 11, 21 are substantially identical, as shown in the three figures, and they are made out of various materials, advantageously by thermoforming with thermoplastic polycarbonate or the like, as is the flexible hinge 40.

In a preferred embodiment, the means 12, 22 for associating one of the plates 11, 21 with a resected end of one of the two bones O1, O2 are constituted by a tab 51, 52, means for securing the tab with the plate, a bone screw 53, 54, and means for associating the tab with the bone screw.

The two bone screws are preferably made of titanium and are self-tapping, thus enabling them to be osteo-integrated in the immediate cavities of the bones, for example phalanges and metacarpal bones in a particularly advantageous application.

In a possible and preferred embodiment, the means for associating said tab with said bone screw are constituted by the fact that the tab 51, 52 is of cylindrical shape and that, in the bone screw, there is made a blind housing 55, 56 of cylindrical shape, the cross-section of this housing being substantially complementary to the cross-section of the tab so that the tab is suitable for sliding in translation therein.

Also, in entirely preferred manner, the tab 51, 52 is in the form of a cylindrical body of revolution so that it is suitable for swiveling in the blind housing 55, 56 about its own longitudinal axis. Most preferably, the two tabs are both in the form of cylindrical bodies of revolution and they are identical.

Each plate, by means of the tab in the form of a cylindrical body of revolution, becomes fitted in the corresponding bone screw, thereby providing a piston effect in translation, and also if necessary in rotation, in order to adjust the position of the plate on the resected face of the bone, since prosthesis needs to work both in distraction and in compression.

As for the means for securing the tab with the plate, they may be of various forms, e.g. being constituted by any one of the following embodiments: making the tab and the plate as a single piece as shown in FIG. 1, or releasably mounting the tab with the plate, e.g. using a dovetail mount as shown in FIG. 3, or by clip fastening, or in analogous manner.

The way in which such a prosthesis is implanted is determined by practitioners and is not described specifically in detail herein, particularly since it does not come within the scope of the protection of the invention.

As shown in FIG. 2, the present invention also provides an instrument 100 for assistance in assembling a prosthesis as defined above.

This instrument comprises a guide 110 having one end 111 including a piece suitable for bearing against the two plates, this piece advantageously including an indentation 112 matching at least a portion of the two plates 11, 21 when they are in the position in which they are suitable for being associated with each other by the flexible hinge 40, a crosspiece 120 extending from side to side in this guide 110 and having a cross-section complementary to the cross-section of the flexible hinge 40, the crosspiece being made in the guide 110 so as to be perfectly in register with the ends of the holes 44, 45 and the slots 46, 47 situated in the first faces of the two plates 11, 21 when the two plates are plugged into their respective indentations, and a pusher 130 for pushing the flexible hinge 40 in translation in the crosspiece 120 in order to position the flexible hinge 40 in cooperation with the two plates 11, 21 when the two plates are plugged into their respective indentations, in such a manner that the two swellings 42, 43 and the flexible strip 41 are received respectively in the two holes 44, 45 and in the two slots 46, 47.

The use and the operation of such an instrument can be deduced without difficulty from the above description. They are therefore not described more fully herein, solely for the purpose of simplifying the present description.

The invention claimed is:

1. A prosthesis for restoring a joint between first and second bones, the prosthesis comprising:
   a first plate;
   a first plate engagement system configured to engage the first plate with a resected end of the first bone;
   a second plate;
   a second plate engagement system configured to engage the second plate with a resected end of the second bone;
   a mounting system configured to mount the two plates pivotally relative to each other about a pivot axis, the mounting system comprising
   a flexible hinge comprising
      a flexible rectangular prism having a longitudinal axis, and
      two closed solids joined respectively with two opposite edges of said flexible rectangular prism so that generator lines of the rectangular prism and generator lines of the two closed solids are substantially parallel to said pivot axis, a height of each of the two closed solids taken along a cross-section defined by a plane, passing through the two closed solids and the rectangular prism and that is perpendicular to the longitudinal axis of the rectangular prism, being greater than a height of the rectangular prism taken along the cross-section;
   a hole defined in each of the two plates, each hole having an end opening out in a first face of the plate in which the hole is made, the two holes having respective shapes complementary to the two respective closed solids; and
   a slot defined in each of the two plates, the slots made in each plate opening out into the hole made in each plate and into a second one of its faces, and including an end opening out into the first face of each plate,
   wherein the flexible hinge and the two plates are mounted in cooperation such that the two closed solids are disposed in the two holes and the flexible rectangular prism is disposed in the two slots wherein each plate is a substantially pyramid shape with square cross-sections, each plate having a cross-section and defined perpendicularly to the generator lines having a substantially triangular shape with one of its vertices having an angle of value greater than ninety degrees.

2. The prosthesis according to claim 1, wherein the slot defined in each plate opens out substantially at said one of the vertices of the triangle and is defined along a height of the triangle.

3. The prosthesis according to claim 2, wherein the two plates are substantially identical.

4. The prosthesis according to claim 1, further comprising at least one piece of reinforcement embedded in the material of the flexible rectangular prism.

5. The prosthesis according to claim 1, wherein the first plate engagement system and the second plate engagement system are each constituted by:
   a tab;
   a securing system configured to secure the tab with each respective plate;
   a self-tapping bone screw; and
   a bone screw engagement system configured to engage the tab with said bone screw.

6. The prosthesis according to claim 5, wherein the tab is cylindrically-shaped, and the bone screw engagement system comprises a cylindrically-shaped blind housing, the cross-section of said blind housing being substantially complementary to the cross-section of said tab so that the tab is slidable in translation in said blind housing.

7. The prosthesis according to claim 6, wherein the tabs are identical and are configured to spin within each respective blind housing about a longitudinal axis.

8. The prosthesis according to claim 1, wherein said one vertex has an angle of value substantially equal to 102 degrees.

\* \* \* \* \*